(12) United States Patent
Berard et al.

(10) Patent No.: US 6,187,130 B1
(45) Date of Patent: Feb. 13, 2001

(54) METHOD OF CREATING A TIP ON A CATHETER

(75) Inventors: John Berard, Plymouth; Jeff Voy Scheinost, Dayton; Thomas Mark Benson, Minneapolis; Diana Moore, Maple Grove, all of MN (US)

(73) Assignee: SciMed Life Systems, Inc., Maple Grove, MN (US)

(*) Notice: Under 35 U.S.C. 154(b), the term of this patent shall be extended for 0 days.

(21) Appl. No.: 09/320,329

(22) Filed: May 26, 1999

(51) Int. Cl.[7] .................................................... B29C 65/02
(52) U.S. Cl. ................... 156/294; 156/304.2; 156/304.6; 264/138; 264/248; 264/254
(58) Field of Search ..................... 264/248, 254, 264/255, 138, 293, 294; 156/158, 304.2, 304.6

(56) References Cited

U.S. PATENT DOCUMENTS

| | | | |
|---|---|---|---|
| 3,470,869 | 10/1969 | Fenton et al. | 128/2 |
| 3,605,750 | 9/1971 | Sheridan et al. | 128/348 |
| 3,725,522 | 4/1973 | Sheridan et al. | 264/138 |
| 3,865,666 | 2/1975 | Shoney | 156/245 |

(List continued on next page.)

FOREIGN PATENT DOCUMENTS

| | | |
|---|---|---|
| 0 437 291 B1 | 7/1991 | (EP) . |
| 0 801 581 B1 | 10/1997 | (EP) . |
| 2 187 670 A | 9/1987 | (GB) . |

OTHER PUBLICATIONS

Carlson, D. Peter et al., "Fluoropolymers, Organic," *Ullmann's Enclyclopedia of Industrial Chemistry*, vol. A 11 (1988) pp. 393–428.

Johnson, R. W., "Paste Extrusion of Filled TFE–Fluorocarbon Resin for Wire Insulations," *SPE Journal*, Feb. 1961, pp. 151–154.

Lontz, John F. et al., "Extrusion Properties of Lubricated Resin From Coagulated Dispersion," *Industrial and Engineering Chemistry*, vol. 44, No. 8, Aug. 1952, pp. 1805–1810.

McCane, Donald I., "Tetrafluoroethylene Polymers," *Encyclopedia of Polymer Science and Technology*, vol. 13 (1970) pp. 623–654.

*Primary Examiner*—Jan H. Silbaugh
*Assistant Examiner*—Stefan Staicovici
(74) *Attorney, Agent, or Firm*—Crompton, Seager & Tufte, LLC

(57) ABSTRACT

A method of forming a tip on a catheter having a elongate shaft. The method includes the step of positioning a first tubular member so that it is overlying the distal portion of the elongate shaft. The method further including the step of positioning a second tubular member so that a proximal end of the second tubular member is proximate a distal end of the first tubular member. The method further includes the step of positioning a third tubular member so that it overlays both the first tubular member and the second tubular member. At least the distal portion of the elongate shaft is then heated, wherein the first tubular member, the second tubular member, and the third tubular member are fused to form a catheter tip affixed to the distal portion of the elongate shaft.

26 Claims, 3 Drawing Sheets

U.S. PATENT DOCUMENTS

| | | | |
|---|---|---|---|
| 3,873,391 | 3/1975 | Plauka et al. | 156/258 |
| 3,959,429 | 5/1976 | Benning | 264/155 |
| 3,962,153 | 6/1976 | Gore | 260/2.5 R |
| 3,985,601 | 10/1976 | Panagrossi | 156/229 |
| 3,989,571 | 11/1976 | Harautuneian | 156/250 |
| 4,085,185 | 4/1978 | Adair | 264/248 |
| 4,093,484 | 6/1978 | Harrison et al. | 156/244.13 |
| 4,207,900 | 6/1980 | Patel et al. | 128/349 B |
| 4,210,478 | 7/1980 | Shoney | 156/242 |
| 4,279,252 | 7/1981 | Martin | 128/349 R |
| 4,284,459 | 8/1981 | Patel et al. | 156/245 |
| 4,323,071 | 4/1982 | Simpson et al. | 128/343 |
| 4,328,056 | 5/1982 | Snooks | 156/242 |
| 4,444,186 | 4/1984 | Wolvek et al. | 128/325 |
| 4,531,943 | 7/1985 | Van Tassel et al. | 604/280 |
| 4,557,781 | 12/1985 | Hoppie | 156/245 |
| 4,563,181 | 1/1986 | Wijayarathna et al. | 604/280 |
| 4,571,240 | 2/1986 | Samson et al. | 604/96 |
| 4,588,399 | 5/1986 | Nebergall et al. | 604/280 |
| 4,596,563 | 6/1986 | Pande | 604/264 |
| 4,636,346 | 1/1987 | Gold et al. | 264/139 |
| 4,655,762 | 4/1987 | Rogers | 604/403 |
| 4,690,175 | 9/1987 | Ouchi et al. | 138/131 |
| 4,737,219 | 4/1988 | Taller et al. | 156/215 |
| 4,753,765 | 6/1988 | Pande | 264/149 |
| 4,778,550 | 10/1988 | Barton et al. | 156/211 |
| 4,806,182 | 2/1989 | Rydell et al. | 156/211 |
| 4,826,480 | 5/1989 | Diaz et al. | 604/49 |
| 4,842,590 | 6/1989 | Tanabe et al. | 604/282 |
| 4,863,442 | 9/1989 | DeMello et al. | 604/282 |
| 4,874,373 | 10/1989 | Luther et al. | 604/164 |
| 4,886,506 | 12/1989 | Lovgren et al. | 604/280 |
| 4,925,710 | 5/1990 | Buck et al. | 428/34.5 |
| 4,950,257 | 8/1990 | Hibbs et al. | 604/265 |
| 4,959,067 | 9/1990 | Muller | 606/190 |
| 5,035,686 | 7/1991 | Crittenden et al. | 604/96 |
| 5,037,404 | 8/1991 | Gold et al. | 604/282 |
| 5,045,072 | 9/1991 | Castillo et al. | 604/280 |
| 5,057,092 | 10/1991 | Webster, Jr. | 604/282 |
| 5,125,913 | 6/1992 | Quackenbush | 604/264 |
| 5,160,559 | 11/1992 | Scovil et al. | 156/83.6 |
| 5,167,647 | 12/1992 | Wijkamp et al. | 604/281 |
| 5,171,232 | 12/1992 | Castillo et al. | 604/280 |
| 5,190,529 | 3/1993 | McCrory et al. | 604/175 |
| 5,199,950 | 4/1993 | Schmitt et al. | 604/95 |
| 5,201,723 | 4/1993 | Quinn | 604/264 |
| 5,217,555 | 6/1993 | Franklin, III et al. | 156/156 |
| 5,221,270 | 6/1993 | Parker | 604/282 |
| 5,234,416 | 8/1993 | Macaulay et al. | 604/282 |
| 5,240,537 | 8/1993 | Bodicky | 156/244.13 |
| 5,254,107 | 10/1993 | Soltesz | 604/282 |
| 5,279,596 | 1/1994 | Castaneda et al. | 604/282 |
| 5,300,032 | 4/1994 | Hibbs et al. | 604/164 |
| 5,312,356 | 5/1994 | Engelson et al. | 604/164 |
| 5,318,032 | 6/1994 | Lonsbury et al. | 128/658 |
| 5,330,444 | 7/1994 | Webler et al. | 604/265 |
| 5,380,301 | 1/1995 | Prichard et al. | 604/281 |
| 5,399,164 | 3/1995 | Snoke et al. | 604/95 |
| 5,441,489 | 8/1995 | Utsumi et al. | 604/280 |
| 5,445,624 | 8/1995 | Jimenez | 604/280 |
| 5,531,685 * | 7/1996 | Hemmer et al. | 604/95 |
| 5,531,721 | 7/1996 | Pepin et al. | 604/282 |
| 5,533,988 | 7/1996 | Dickerson et al. | 604/282 |
| 5,542,924 | 8/1996 | Snoke et al. | 604/95 |
| 5,545,149 | 8/1996 | Brin et al. | 604/265 |
| 5,545,151 | 8/1996 | O'Connor et al. | 604/282 |
| 5,558,737 * | 9/1996 | Brown et al. | 156/172 |
| 5,569,218 | 10/1996 | Berg | 604/282 |
| 5,584,821 | 12/1996 | Hobbs et al. | 604/280 |
| 5,762,637 | 6/1998 | Berg et al. | 604/264 |
| 5,811,043 | 9/1998 | Horrigan et al. | 264/138 |
| 5,836,925 | 11/1998 | Soltesz | 604/280 |
| 5,951,929 * | 9/1999 | Wilson | 264/139 |
| 6,103,037 * | 8/2000 | Wilson | 156/158 |
| B1 4,323,071 | 5/1990 | Simpson et al. | 128/343 |

* cited by examiner

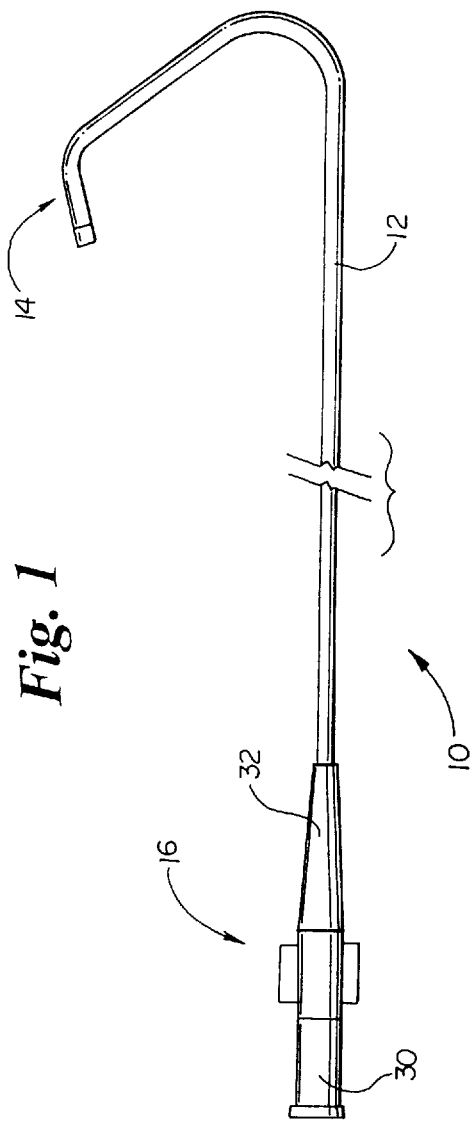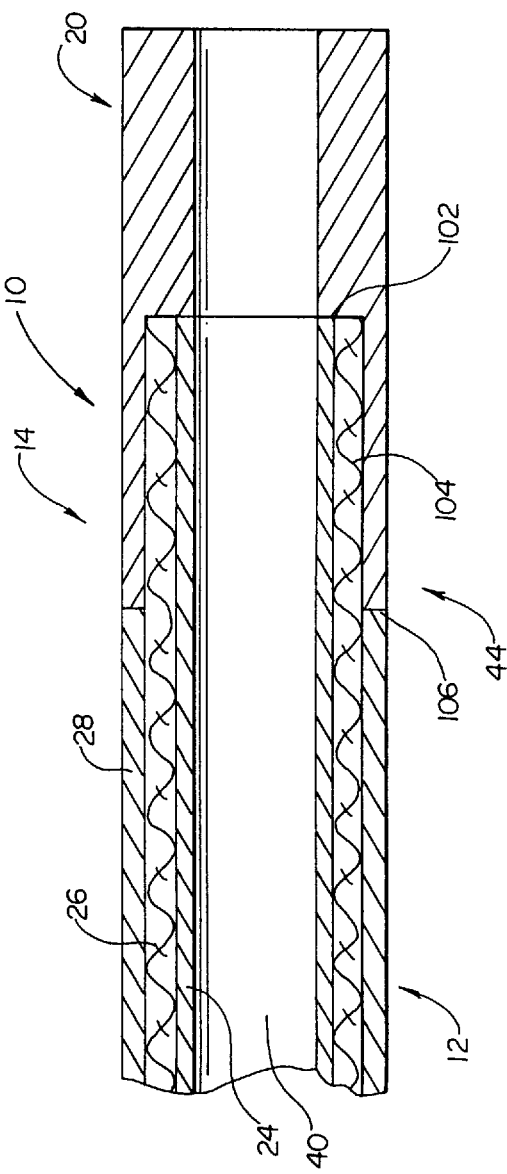

METHOD OF CREATING A TIP ON A CATHETER

FIELD OF THE INVENTION

The present invention relates generally to catheters for performing medical procedures. More particularly, the present invention relates to guide catheters for use in an angioplasty procedure.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened.

The most widely used form of angioplasty makes use of a guide catheter positioned within the vascular system of a patient. The guiding catheter assists in transporting the balloon dilation catheter to the restriction in the diseased vessel. During this procedure, the distal end of the guide catheter is typically inserted into the femoral artery located near the groin of the patient. The guide catheter is urged through the vasculature of the patient until its distal end is proximate the restriction. In many cases, the distal end of the guide catheter is positioned in the ostium of the coronary artery. The balloon catheter may then be fed through a lumen in the guide catheter.

The guide catheter must possess a level of rigidity which will allow it to be passed through the vascular system without folding or buckling. Because the guide catheter possesses this level of rigidity, it is desirable to incorporate an atraumatic tip on the distal end of the guide catheter to avoid injury to the walls of the blood vessels.

SUMMARY OF THE INVENTION

The present invention relates generally to catheters for performing medical procedures. More particularly, the present invention relates to guide catheters for use in an angioplasty procedure. A guide catheter in accordance with the present invention includes an elongate shaft. A hub is preferably affixed to the proximal end of the elongate shaft. In the catheter of the present invention, an atraumatic tip is affixed to the distal end of the elongate shaft.

A method of forming an atraumatic tip in accordance with the present invention typically begins with the step of providing an elongate shaft. A joining portion of generally reduced diameter and desired axial length is formed or included proximate a distal end of the elongate shaft. A variety of manufacturing methods may be used to form the joining portion of the elongate shaft including using a thinner wall extrusion segment, material forming processes and material removal processes.

After the joining portion has been formed or otherwise included on the elongate shaft, the joining portion is inserted into the lumen of a first tubular member. The first tubular member is then positioned so that a proximal end thereof is adjacent and abutting a step in the elongate shaft corresponding to the proximal end of the joining portion of the elongate shaft. The first tubular member preferably has a lumen diameter about equal to the outside diameter of the joining portion of the shaft to be disposed thereon.

A mandrel is positioned so that a portion of the mandrel is disposed inside the lumen of the elongate shaft, and the remainder of the mandrel extends distally from the distal portion of the elongate shaft. The mandrel may then be inserted into the lumen of a second tubular member. The second tubular member is slid completely onto the mandrel so that a proximal end of the second tubular member is proximate and preferably abutting the distal end of the first tubular member and the distal end of the elongate shaft. The second tubular member preferably has a lumen diameter about equal to the mandrel diameter.

The next step in a method in accordance with the present invention is positioning a third tubular member so that it overlays both the first tubular member and the second tubular member. The proximal end of the third tubular member is positioned proximate the step in the elongate shaft corresponding to the proximal end of the joining portion of the elongate shaft. The length of the third tubular member is preferably substantially equal to the combined lengths of the first tubular member and the second tubular member so that the distal end of the third tubular member is generally aligned with the distal end of the second tubular member.

In one method in accordance with the present invention, the distal portion of the elongate shaft is overlaid with a sleeve. The first tubular member, the second tubular member, the third tubular member, and the joining portion of the elongate shaft are all disposed in a lumen of the sleeve. In a presently preferred method, the sleeve is comprised of heat shrink tubing. After placing the sleeve in the desired position, heat is applied to the sleeve causing it to shrink. After shrinking, the diameter of the sleeve lumen is substantially equal to the outer diameter of both the third tubular member and the elongate shaft.

The first tubular member, the second tubular member, the third tubular member, and the distal portion of the elongate shaft are heated to an elevated temperature. A number of methods may be used to heat the assembly including convection, conduction and radiation.

In a presently preferred method in accordance with the present invention, the first tubular member, the second tubular member, and the third tubular member are heated to a temperature at or above their melting point, causing them all to fuse together forming an integral distal tip. The elevated temperature also causes the distal tip to be securely bonded to the distal portion or joining portion of the elongate shaft.

BRIEF DESCRIPTION OF THE DRAWINGS

FIG. 1 is a plan view of a guide catheter in accordance with a preferred embodiment of the present invention;

FIG. 2 is a sectional plan view of a catheter distal portion detailing the final assembly of the tip portion of the present invention;

DETAILED DESCRIPTION OF THE INVENTION

Figure 3:
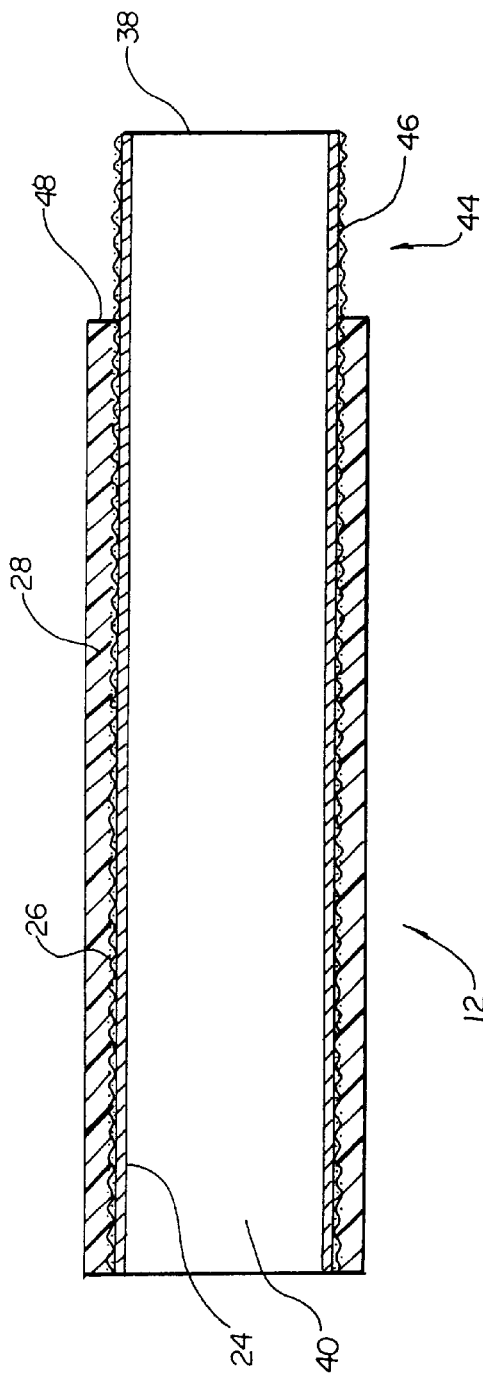
FIG. 3 is a sectional plan view of a tubular member having a reduced diameter joining portion disposed at the distal end thereof.

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

FIG. 1 is a plan view of a guiding catheter 10. Guiding catheter 10 includes an elongate shaft 12, a distal portion 14, and a proximal portion 16. Proximal portion 16 of catheter 10 includes a hub 30 and a strain relief 32. Hub 30 and strain relief 32 enable a physician to connect other devices to guiding catheter 10. Hub 30 and strain relief 32 also provide a convenient place for a physician to apply longitudinal or rotational forces in order to manipulate guiding catheter 10. Proximate to the distal end of catheter 10 is a distal tip 20. In a presently preferred embodiment, distal tip 20 is generally softer and more flexible than elongate shaft 12.

FIG. 2 is an enlarged sectional view of a distal portion 14 of the catheter 10 of FIG. 1. In a presently preferred embodiment, catheter 10 is a guiding catheter, however, it should be understood that catheter 10 may be another type of catheter without departing from the spirit or scope of this invention. A distal portion 14 of catheter 10 includes a distal tip 20.

Catheter 10 also includes an elongate shaft 12 having a lumen 40 and an outer surface 42. Elongate shaft 12 is comprised of an inner tube 24 which is overlaid by a support member 26. An outer tube 28 overlays support member 26.

As best seen in FIG. 3, prior to adding the distal tip 20, elongate shaft 12 includes a distal end 38 and a joining portion 44 of selected length proximate distal end 38. Bonding portion 44 includes a joining surface 46. The outer diameter of joining surface 46 is generally smaller than the outer diameter of outer tube 28 creating a step 48 in outer tube 28.

Referring again to FIG. 2, distal tip 20 is preferably bonded to elongate shaft 12 at a first butt joint 102, a lap joint 104, and a second butt joint 106. First butt joint 102 is formed between distal tip 20 and distal end 38 of elongate shaft 12 distal tip 20. Lap joint 104 is formed between distal tip 20 and joining surface 46 of elongate shaft 12. Second butt joint 106 is formed between distal tip 20 and step 48 of outer tube 28.

In a presently preferred embodiment, inner tube 24 is comprised of PTFE (polytetrafluoroethylene). PTFE is a preferred material because it creates a smooth, low-friction surface for the passage of other devices through the catheter. Also in a preferred embodiment, support member 26 is a stainless steel wire, wound in a braided pattern around inner tube 24. Those with skill in the art will appreciate that other embodiments of support member 26 are possible without deviating from the spirit and scope of the present invention. For example, support member 26 may be comprised of a woven polymer fabric. By way of a second example, support member 26 may be comprised of polymer fibers wound in a braided pattern.

In a preferred embodiment, outer tube 28 is comprised of polyether block amide (PEBA). Polyether block amide is commercially available from Atomchem Polymers of Birsdsboro Pennsylvania under the trade name PEBAX. Outer tube 28 may be fabricated using an extrusion process. In this process, molten PEBA is extruded onto combined layers of inner tube 24 and support member 26. The material of outer tube 28 fills in any interstitial spaces in support member 26.

Outer tube 26 may be comprised of other materials without departing from the spirit of scope of this invention. Examples of materials which may be suitable in some applications include: polyethylene (PE), polypropylene (PP), polyvinylchloride (PVC), polyurethane, and polytetrafluoroethylene (PTFE).

As described previously, the material of distal tip 20 is preferably softer than the material of outer layer 26. In a preferred embodiment, both distal tip 20 and outer layer 26 are comprised of polyether block amide (PEBA). However, in this preferred embodiment, distal tip 20 is comprised of a PEBA material with a lower durometer than that of outer layer 26.

It should be understood that radiopaque loading agents may be added to the material of distal tip 20 without deviating from the spirit or scope of the present invention. The material of distal tip 20 may also include a color pigment. The radiopaque material makes distal tip 20 more easily visualized when using radiographic and/or fluoroscopy techniques. In a preferred embodiment, distal tip 20 is comprised of a PEBA polymer having a durometer of about 35 to 40 Shore-D and loaded with a radiopaque material.

Figure 4:
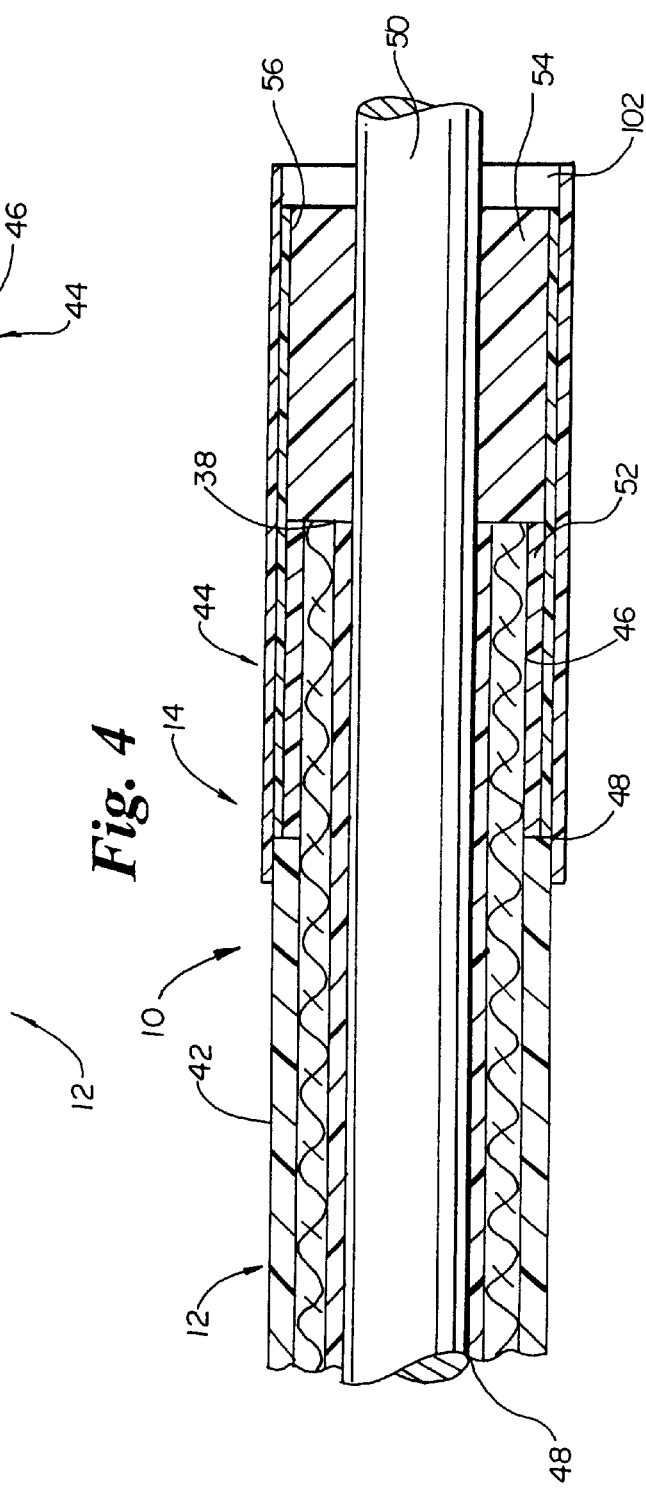
FIG. 4 is a sectional plan view of the tubular member of FIG. 3 having tip members and a heat shrink sleeve disposed on the joining portion.

FIG. 4 is an enlarged sectional view of an assembly illustrating a preferred method of manufacturing the present invention. In FIG. 4, the distal portion of catheter 10 is shown in a partially assembled state. The assembly of FIG. 4 includes elongate shaft 12 having a lumen 40 and an outer surface 42. Elongate shaft 12 also includes a distal end 38 and a joining portion 44 proximate the distal end 38. Joining portion 44 has a joining surface 46. The outer diameter of joining surface 46 is generally smaller than the outer diameter of outer surface 42 of outer tube 28 creating a step 48 in elongate shaft 12.

In FIG. 4, a mandrel 50 has been positioned so that it is partially disposed inside lumen 40 of elongate shaft 12. The remainder of mandrel 50 extends distally away from the distal end of elongate shaft 12.

Figure 7:
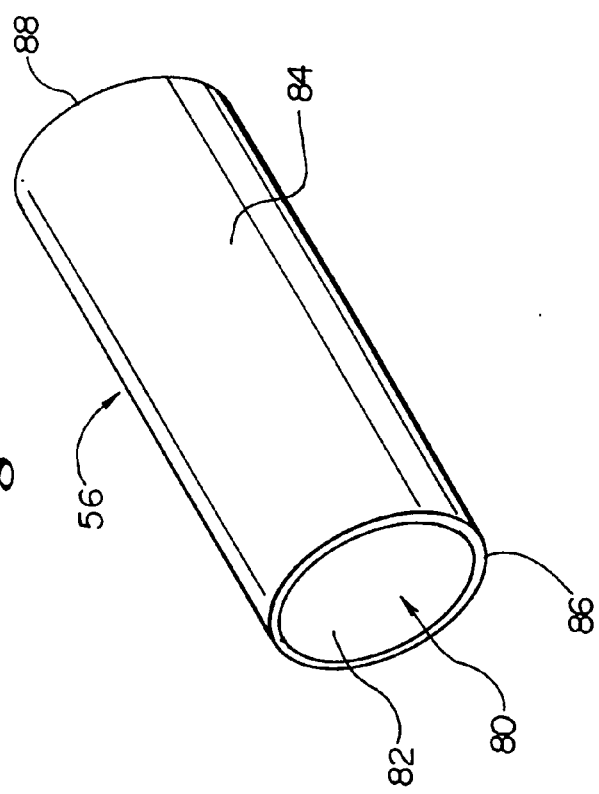
FIG. 7 is a perspective view of a third tubular member sized for placement over the first and second tubular members.
Figure 6:
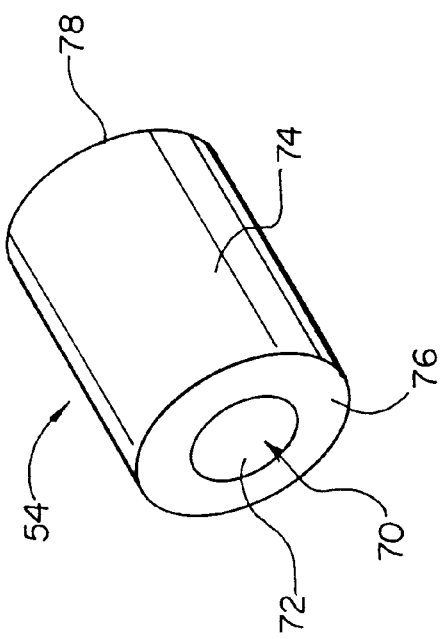
FIG. 6 is a perspective view of a second tubular member sized for placement over a mandrel in abutment with the first tubular member.
Figure 5:
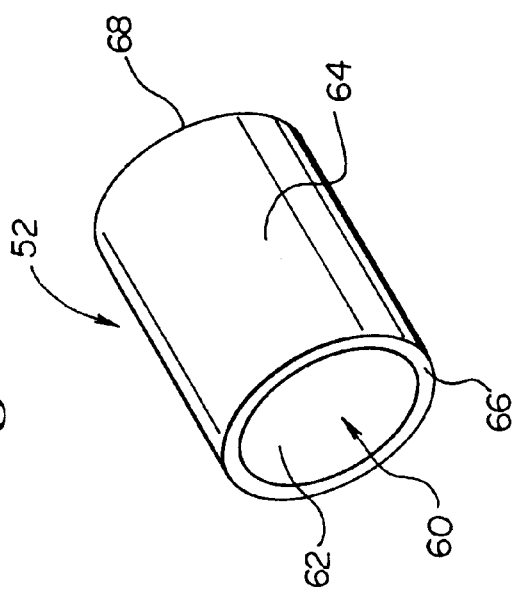
FIG. 5 is a perspective view of a first tubular member for placement over the joining portion.

The assembly of FIG. 4 includes a first tubular member 52, a second tubular member 54, and a third tubular member 56. Tubular members 52, 54, and 56 are best shown individually in FIGS. 5, 6, and 7 respectively. First tubular member 52 includes a proximal end 66, a distal end 68, an outer surface 64, and a lumen 60 having a lumen surface 62. Likewise, second tubular member 54 includes a proximal end 76, a distal end 78, an outer surface 74, and a lumen 70 having a lumen surface 72. Finally, third tubular member 56 includes a proximal end 86, a distal end 88, an outer surface 84, and a lumen 80 having a lumen surface 82.

In the assembly of FIG. 4, joining portion 44 of elongate shaft 12 has been inserted into lumen 60 of first tubular member 52. As seen in FIG. 4, the diameter of joining surface 46 is substantially equal to the diameter of lumen 60 of first tubular member 52. Also as seen in FIG. 4, first tubular member 52 is positioned so that proximal end 66 thereof is adjacent or abutting step 48 of elongate shaft 12.

In the assembly of FIG. 4, mandrel 50 has been inserted into lumen 70 of second tubular member 54. Second tubular member 54 has been slid completely onto mandrel 50 so that proximal end 76 of second tubular member 54 is proximate distal end 68 of first tubular member 52 and distal end 38 of elongate shaft 12, preferably abutting both first tubular member 52 and distal end 38. The outer diameter of second tubular member 54 is substantially equal to the outer diameter of first tubular member 52. Further, the outside diameter of both first tubular member 52 and second tubular member 54 is preferably less than the outside diameter of elongate shaft 12. As shown in FIG. 4, lumen 70 of second tubular member 54 is generally in axial alignment with lumen 40 of elongate shaft 12. Mandrel 50 is adapted to assist in accomplishing this axial alignment.

Third tubular member 56 is positioned so that it overlays both first tubular 52 member and second tubular member 54. The diameter of lumen 80 of third tubular member 56 is substantially equal to the outer diameters of both first tubular member 52 and second tubular member 54. The outer diameter of third tubular member 56 is substantially equal to the outer diameter of elongate shaft 12. Proximal end 86 of third tubular member 56 is positioned proximate or in abutment with step 48 of elongate shaft 12. The length of third tubular member 56 is preferably substantially equal to the combined lengths of first tubular member 52 and second tubular member 54 so that distal end 88 of third tubular member 56 is generally aligned with distal end 78 of second tubular member. It is, however, recognized that these lengths need not be equal during manufacture, as their lengths may be trimmed after assembly.

The assembly of FIG. 4 also includes a sleeve 102 having a lumen 110. Sleeve 102 is positioned so that if overlays the distal portion of elongate shaft 12. As shown in FIG. 4, first tubular member 52, second tubular member 54, third tubular member 56, and joining portion 38 of elongate shaft 12 are all disposed in lumen 110 of sleeve 102.

In a presently preferred embodiment, sleeve 102 is comprised of polytetrafluoroethylene (PTFE). Alternatively, an FEP shrink wrap sleeve may be utilized. It is preferred that the sleeve provide a substantially non-stick surface, which is provided by a fluoropolymer material. In a presently preferred embodiment, sleeve 102 is comprised of PTFE heat shrink tubing. Suitable PTFE heat shrink tubing is commercially available from Zeus Industries of Orangeburg, S.C. and Raychem Corporation of Menlo Park, Calif.

Having thus described the figures, a method of forming a distal tip on a catheter may now be described with reference to FIGS. 2, 3, and 4. In a method in accordance with the 5 present invention the creation of a tip on distal portion 14 of catheter 10 typically begins with the step of providing a reduced area or joining portion on the distal end of elongate shaft 12.

A variety of manufacturing methods may be used to form joining portion 44 of elongate shaft 12 including using a thinner wall extruded section, material forming processes and material removal processes. Examples of material removal processes which may be acceptable in some applications include turning on a lathe and centerless grinding. An example of a material forming process which may be acceptable in some applications is forging by compressing joining region 52 of tubular section 50 in a heated tool of the desired shape.

After joining portion 44 has been formed on elongate shaft 12, joining portion 44 is inserted into lumen 60 of first tubular member 52. First tubular member 52 is then positioned so that proximal end 66 thereof is adjacent or abutting step 48 of elongate shaft 12.

A mandrel 50 is positioned so that a portion of the mandrel is disposed inside the lumen 40 of the elongate shaft 12, and the remainder of the mandrel 50 extends from the distal portion of the elongate shaft 12. Mandrel 50 may now be inserted into lumen 70 of second tubular member 54. Second tubular member 54 is slid completely onto mandrel 50 so that proximal end 76 of second tubular member 54 is proximate or abutting distal end 68 of first tubular member 52 and distal end 38 of elongate shaft 12. As shown in FIG. 4, lumen 70 of second tubular member 54 is generally in axial alignment with lumen 40 of elongate shaft 12. Mandrel 50 is adapted to assist in accomplishing this axial alignment.

The next step in a method in accordance with the present invention is positioning third tubular member 56 so that it overlays both first tubular member 52 and second tubular member 54. Proximal end 86 of third tubular member 56 is positioned proximate to or abutting step 38 of elongate shaft 12. The length of third tubular member 56 is substantially equal to the combined lengths of first tubular member 52 and second tubular member 54 so that distal end 88 of third tubular member 56 is generally aligned with distal end 78 of second tubular member.

The distal portion of elongate shaft 12 is then overlaid with sleeve 102. As shown in FIG. 4, first tubular member 52, second tubular member 54, third tubular member 56, and joining portion 38 of elongate shaft 12 are all disposed in lumen 110 of sleeve 102. In a presently preferred method, sleeve 102 is comprised of heat shrink tubing. After placing sleeve 102 in the desired position, heat is applied to sleeve 102 causing it to shrink. After shrinking, the diameter of lumen 110 of sleeve 102 is substantially equal to the outer diameter of both third tubular member 56 and elongate shaft 12. A number of methods may be used to heat sleeve 102 including convection, conduction and radiation. In one presently preferred embodiment, sleeve 102 is heated by directing a flow of hot air from a hot air gun so that it impinges on sleeve 102. Hot air guns suitable for this application are commercially available from Leister Elektro-Geratebau of Lucerne, Switzerland. Alternatively, a heated die having two halves can be utilized The first tubular member, the second tubular member, the third tubular member, and the distal portion of the elongate shaft are heated to an elevated temperature. A number of methods may be used to heat the assembly including convection, conduction and radiation. An example of heating with radiant energy is directing infra-red energy from an infrared heat source at the assembly. Infra-red energy sources suitable for this process are commercially available from Research Incorporated of Minnetonka, Minn. A second example of heating with radiant energy is exposing the regions to be heated to radio frequency energy. An example of heating with convection includes directing a flow of hot air from a hot air gun so that it impinges on the assembly. Hot air guns suitable for this application are commercially available from Leister Elektro-Geratebau of Lucerne, Switzerland. A second example of heating with convection includes placing the portion being heated in a temperature chamber. Temperature chambers suitable for this process are commercially available from Thermotron Corporation of New Holland, Mich.

An example of heating with conduction is placing a heated tool in direct contact with the assembly. Suitable heated tools may be comprised of a number of materials including stainless steel. Electric heaters suitable for heating a heated tool are commercially available from Watlow Incorporated of St. Louis, Mo.

In a presently preferred method in accordance with the present invention, the first tubular member, the second tubular member, and the third tubular member are heated to a temperature at or above their melting point, causing them all to fuse together forming distal tip 20. The elevated temperature also causes distal tip 20 to be securely bonded to the distal portion of the elongate shaft. As may be seen in FIG. 4, distal tip 20 is securely bonded to elongate shaft 12 at first butt joint 60, lap joint 62, and second butt joint 64. Further, in preferred embodiments, the distal tip components, including the first tubular member 52, the second tubular member 54 and third tubular member 56, are made from the same material so that when they are heated, they form an integral tip 20 with no bond sites between tip components.

Having formed distal tip 20, the assembly is then allowed to cool. The assembly may be submersed in a relatively cool fluid to speed cooling of the assembly. Examples of fluids which may be suitable for some applications include water and air. Relatively cool air may also be impinged onto the assembly. Cold air generators suitable for this purpose are commercially available from ITW Vortec of Cincinnati, Ohio and Exair Corporation of Cincinnati, Ohio.

After the assembly has cooled, sleeve 102 is removed. This may be accomplished by scoring sleeve 102 with a cutting tool, and peeling it away from distal tip 20 and elongate shaft 12. In a presently preferred method, sleeve 102 is comprised of polytetrafluoroethylene (PTFE). PTFE is preferred because it provides a substantially non-stick surface. This substantially non-stick surface aids in the removal of sleeve 102 from distal tip 20 and elongate shaft 12.

The mandrel 50 is then removed from the lumen of elongate shaft 12. In a presently preferred method, the outer surface of mandrel 50 includes polytetrafluoroethylene (PTFE). PTFE is preferred because it provides a substantially non-stick surface. This substantially non-stick surface aids in the removal of mandrel 50 from catheter 100.

It should be understood that steps may be omitted from this process without deviating from the spirit or scope of the invention. For example, alternate methods have been envisioned, in which the use of mandrel 50 and/or sleeve 102 is not required.

Having thus described the preferred embodiments of the present invention, those of skill in the art will readily appreciate that yet other embodiments may be made and used within the scope of the claims hereto attached.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method of forming a tip on a catheter having an elongate shaft, the method comprising the steps of:
   providing an elongate shaft having an outer surface, a distal portion, and a lumen extending longitudinally therethrough;
   providing a first tubular member having an inner surface, an outer surface, and a distal end;
   providing a second tubular member having a proximal end, and an outer surface;
   providing a third tubular member having an inner surface;
   positioning the first tubular member so that it overlays the distal portion of the elongate shaft such that the inner surface of the first tubular member is proximate the outer surface of the elongate shaft;
   positioning the second tubular member so that the proximal end of the second tubular member is proximate the distal end of the first tubular member and a lumen of the second tubular member is in axial alignment with the lumen of the elongate shaft;
   positioning the third tubular member so that it overlays both the first tubular member and the second tubular member such that the inner surface of the third tubular member is proximate the outer surface of the first tubular member and the outer surface of the second tubular member; and
   fusing the first tubular member, the second tubular member, and the third tubular member to form the catheter tip.

2. The method of claim 1, wherein the first tubular member, the second tubular member, and the third tubular member are all comprised of a thermoplastic material.

3. The method of claim 1, wherein the first tubular member, the second tubular member, and the third tubular member are all comprised of the same material.

4. The method of claim 1, wherein the first tubular member, the second tubular member, and the third tubular member are all comprised of polyether block amide.

5. A method of forming a tip on a catheter having an elongate shaft, the method comprising the steps of:
   providing an elongate shaft having a distal portion including a distal end, a proximal end, and a lumen extending between the distal end and the proximal end thereof;
   the elongate shaft further including a joining region having a proximal end, a distal end, and a joining surface extending therebetween;
   providing a first tubular member having a proximal end, a distal end, and a lumen extending therebetween;
   providing a second tubular member having a proximal end, a distal end, and a lumen extending therebetween;
   providing a third tubular member having a proximal end, a distal end, and a lumen extending therebetween;
   inserting a mandrel into the lumen of the elongate shaft so that a portion of the mandrel extends distally from the distal portion of the elongate shaft;
   inserting the distal end of the elongate shaft into the lumen of the first tubular member so that the first tubular member is disposed about the joining portion of the elongate shaft;
   inserting the mandrel into the lumen of the second tubular member and positioning the proximal end of the second tubular member adjacent to the distal end of the first tubular member and having the lumen of the second tubular member in axial alignment with the lumen of the elongate shaft;
   sliding the third tubular member over the first and second tubular members;
   heating the first tubular member, the second tubular member, the third tubular member, and the distal portion of the elongate shaft, wherein the first tubular member, the second tubular member, and the third tubular member are fused to form the catheter tip affixed to the distal portion of the elongate shaft; and
   removing the mandrel from the lumen of the elongate shaft.

6. The method of claim 5, wherein the first tubular member, the second tubular member, and the third tubular member are all comprised of a thermoplastic material.

7. The method of claim 5, wherein the first tubular member, the second tubular member, and the third tubular member are all comprised of the same material.

8. The method of claim 5, wherein the first tubular member, the second tubular member, and the third tubular member are all comprised of polyether block amide.

9. The method of claim 5, wherein an outer diameter of the joining portion of the elongate shaft is substantially equal to the diameter of the lumen of the first tubular member.

10. The method of claim 5, further including the step of surrounding the distal portion of the elongate shaft with a sleeve.

11. The method of claim 5, wherein an outer diameter of the mandrel is substantially equal to the diameter of the lumen of the elongate shaft.

12. The method of claim 5, wherein an outer diameter of the mandrel is substantially equal to the diameter of the lumen of the second tubular member.

13. The method of claim 5, wherein the diameter of the lumen of the second tubular member is substantially equal to the diameter of the lumen of the elongate shaft.

14. The method of claim 5, wherein an outer diameter of the first tubular member is substantially equal to an outer diameter of the second tubular member.

15. The method of claim 5, wherein an outer diameter of the first tubular member is substantially equal to a diameter of the lumen of the third tubular member.

16. The method of claim 5, wherein an outer diameter of the second tubular member is substantially equal to a diameter of the lumen of the third tubular member.

17. The method of claim 5, wherein an outer diameter of the third tubular member is substantially equal to an outer diameter of the elongate shaft.

18. The method of claim 5, wherein the step of heating the first tubular member, the second tubular member, the third tubular member, and the distal portion of the elongate shaft includes placing the first tubular member, the second tubular member, the third tubular member, and the distal portion of the elongate shaft inside a heated chamber.

19. A method of forming a tip on a catheter having a elongate shaft, the method comprising the steps of:
    providing a elongate shaft having a proximal portion, a distal portion, and a lumen extending longitudinally therethrough;
    positioning a first tubular member so that it is overlying the distal portion of the elongate shaft;
    positioning a second tubular member so that a proximal end of the second tubular member is proximate a distal end of the first tubular member and a lumen of the second tubular member is in axial alignment with the lumen of the elongate shaft;
    positioning a mandrel so that a portion of the mandrel is disposed inside a lumen of the second tubular member and a portion of the mandrel is disposed inside the lumen of the elongate shaft;
    positioning a third tubular member so that it overlays both the first tubular member and the second tubular member;
    surrounding the distal portion of the elongate shaft with a shrink tube member;
    applying heat to the shrink tube member, whereby the shrink tube member contracts;
    heating at least the distal portion of the elongate shaft, wherein the first tubular member, the second tubular member, and the third tubular member are fused to form the catheter tip affixed to the distal portion of the elongate shaft;
    removing the shrink tube member; and
    removing the mandrel from the lumen of the elongate shaft.

20. The method of claim 19, wherein the shrink tube member includes a fluoropolymer material.

21. The method of claim 19, wherein the mandrel includes a fluoropolymer material.

22. The method of claim 19, wherein the step of heating at least the distal portion of the elongate shaft includes placing the distal portion of the shaft inside a heated chamber.

23. The method of claim 19, wherein the first tubular member, the second tubular member, and the third tubular member are all comprised of a thermoplastic material.

24. The method of claim 19, wherein the first tubular member, the second tubular member, and the third tubular member are all comprised of the same material.

25. The method of claim 19, wherein the first tubular member, the second tubular member, and the third tubular member are all comprised polyether block amide.

26. The method of claim 19, further including the step of removing material from an outer surface of the elongate shaft.

* * * * *